United States Patent
Crnkovich et al.

(10) Patent No.: US 10,426,881 B2
(45) Date of Patent: Oct. 1, 2019

(54) ENHANCED BACKFLOW PREVENTION IN A HEMODIALYSIS DEVICE

(71) Applicant: Fresenius Medical Care Holdings, Inc., Waltham, MA (US)

(72) Inventors: Marty Crnkovich, Walnut Creek, CA (US); Roland Levin, San Ramon, CA (US); Fei Wang, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 194 days.

(21) Appl. No.: 15/411,606

(22) Filed: Jan. 20, 2017

(65) Prior Publication Data
US 2018/0207340 A1     Jul. 26, 2018

(51) Int. Cl.
*A61M 1/16*     (2006.01)

(52) U.S. Cl.
CPC .......... *A61M 1/169* (2013.01); *A61M 1/1629* (2014.02); *A61M 1/1658* (2013.01); *A61M 1/1668* (2014.02); *A61M 1/1688* (2014.02); *A61M 1/1694* (2013.01); *A61M 2205/18* (2013.01)

(58) Field of Classification Search
CPC .............. A61M 1/1629; A61M 1/1658; A61M 1/1668; A61M 1/1688; A61M 1/169; A61M 1/1694; A61M 2205/18
See application file for complete search history.

(56) References Cited

U.S. PATENT DOCUMENTS

| | | | |
|---|---|---|---|
| 4,158,034 A | 6/1979 | Riede et al. | |
| 4,166,031 A | 8/1979 | Hardy | |
| 4,773,991 A | 9/1988 | Aid | |
| 5,725,773 A | 3/1998 | Polaschegg | |
| 6,861,033 B2 | 3/2005 | Mullins et al. | |
| 8,425,767 B2 | 4/2013 | Fava et al. | |
| 8,834,718 B2 | 9/2014 | Randall et al. | |
| 2014/0174698 A1 | 6/2014 | Ritter et al. | |
| 2015/0005699 A1 | 1/2015 | Burbank et al. | |
| 2016/0356874 A1 | 12/2016 | Wang et al. | |

OTHER PUBLICATIONS

International Search Report and Written Opinion dated May 29, 2018, for PCT/US18/14497 (20 pages).

*Primary Examiner* — John Kim (57) ABSTRACT

A hemodialysis system according to an embodiment of the present invention includes a hydrochamber, and a water circuit for water to flow from an external water source into the hydrochamber via a water inlet valve. The hemodialysis system further includes a spent dialysate circuit for a disinfecting agent to flow to the hydrochamber via a recirculation valve during a disinfectant operation, and a drain valve disposed in the spent dialysate circuit. During the disinfectant operation, the hemodialysis system is adapted to replace a volume of the disinfecting agent exiting the spent dialysate circuit via the drain valve with an equal volume of water via the water inlet valve. The recirculation valve is directly connected to the hydrochamber such that in response to a pressure drop at the external water source, the disinfecting agent is prevented from backflowing through the water inlet valve.

14 Claims, 9 Drawing Sheets

ENHANCED BACKFLOW PREVENTION IN A HEMODIALYSIS DEVICE

FIELD OF THE DISCLOSURE

The disclosure generally relates to a system and method for enhanced backflow prevention in a hemodialysis device, and more particularly to backflow prevention during a disinfectant operation in a hemodialysis device such as a chemical disinfection.

BACKGROUND OF THE INVENTION

Medical devices involving fluid flow typically include a fluid flow path for a disinfectant operation such as a chemical disinfection. A hemodialysis device can function in place of a kidney by filtering waste, salt, and fluid from a patient's blood when the patient's kidneys do not function properly. To ensure the flow paths are properly disinfected for patient use, a chemical wash flows a disinfectant through the flow path. It is extremely critical that hemodialysis devices do not permit contamination of a chemical wash into a flow path containing fluid that may interact with a patient.

During a dialysis operation, a valve in a spent dialysate circuit is always closed, thereby preventing any potential contamination from the spent dialysate to the fresh water inlet. Additionally, an airgap between a water inlet valve and a hydrochamber prevents any patient contamination if there is an external loss of water pressure.

During a chemical disinfection operation, a valve is opened so that a chemical disinfectant flows from the spent dialysate side to the hydrochamber. A drain valve opens at a periodic time interval to disinfect the drain line, and fresh water flows through the water inlet valve to replace the volume emptied out the drain valve. During normal operation, the water circuit is under positive pressure, so water flows into the water inlet valve, and disinfectant is prevented from backflowing through the water inlet valve.

If an external water source fails, the water is no longer under positive pressure, and the chemical disinfectant has a path for potential backflow through the water inlet valve. Although risk to the patient is remote, a solution is needed to prevent potential backflow contamination to ensure patient safety.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In an embodiment, a hemodialysis system may comprise a hydrochamber adapted to heat and remove air from water and to provide backflow protection, a water circuit for water to flow from an external water source into the hydrochamber via a water inlet valve, a spent dialysate circuit for a disinfecting agent to flow to the hydrochamber via a recirculation valve during a disinfectant operation, and a drain valve disposed in the spent dialysate circuit. During the disinfectant operation, the hemodialysis system may be adapted to replace a volume of the disinfecting agent exiting the spent dialysate circuit via the drain valve with a substantially equal volume of water via the water inlet valve. The recirculation valve may be directly connected to the hydrochamber such that in response to a pressure drop at the external water source, the disinfecting agent is prevented from back-flowing through the water inlet valve.

In an embodiment, a method for preventing contamination in a hemodialysis device may comprise circulating water in a water circuit from an external water source to a hydrochamber via a water inlet valve, circulating a disinfecting agent in a spent dialysate circuit into the hydrochamber via a recirculation valve during a disinfectant operation, selectively opening a drain valve to flow a volume of the disinfecting agent through the drain valve out of the hemodialysis device, and selectively opening the water inlet valve to replace the volume of the disinfecting agent. The recirculation valve may be directly connected to the hydrochamber, such that in response to a pressure drop at the external water source, the disinfecting agent is prevented from back-flowing through the water inlet valve.

In an embodiment, a hemodialysis device for preventing backflow contamination during a loss of pressure at an external water source may comprise a water inlet valve in a water circuit for water to flow to a hydrochamber from the external water source, a recirculation valve in a fluid circuit for a disinfecting agent to flow to the hydrochamber during a disinfectant operation, a dual valve manifold, the dual valve manifold including a first channel with a first end port, and a second channel with a second end port, the first end port of the first valve line connecting to the water inlet valve, and the second end port of the second channel connecting to the recirculation valve. The first channel and the second channel may be separate channels in the dual valve manifold such that the flow paths are isolated. The recirculation valve may be directly connected to the hydrochamber, such that in response to the pressure loss at the external water source, the disinfecting agent is prevented from back-flowing through the water inlet valve.

In an embodiment, a method for preventing contamination in a hemodialysis device may comprise maintaining circulation of water in a water circuit from an external water source to a hydrochamber via a water inlet valve during a disinfectant operation, and isolating a flow of an agent from water in the water circuit leading to the external water source, such that in response to a pressure drop at the external water source, the agent is prevented from flowing into the external water source.

BRIEF DESCRIPTION OF THE DRAWINGS

By way of example, specific embodiments of the disclosed device will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Figure 1:
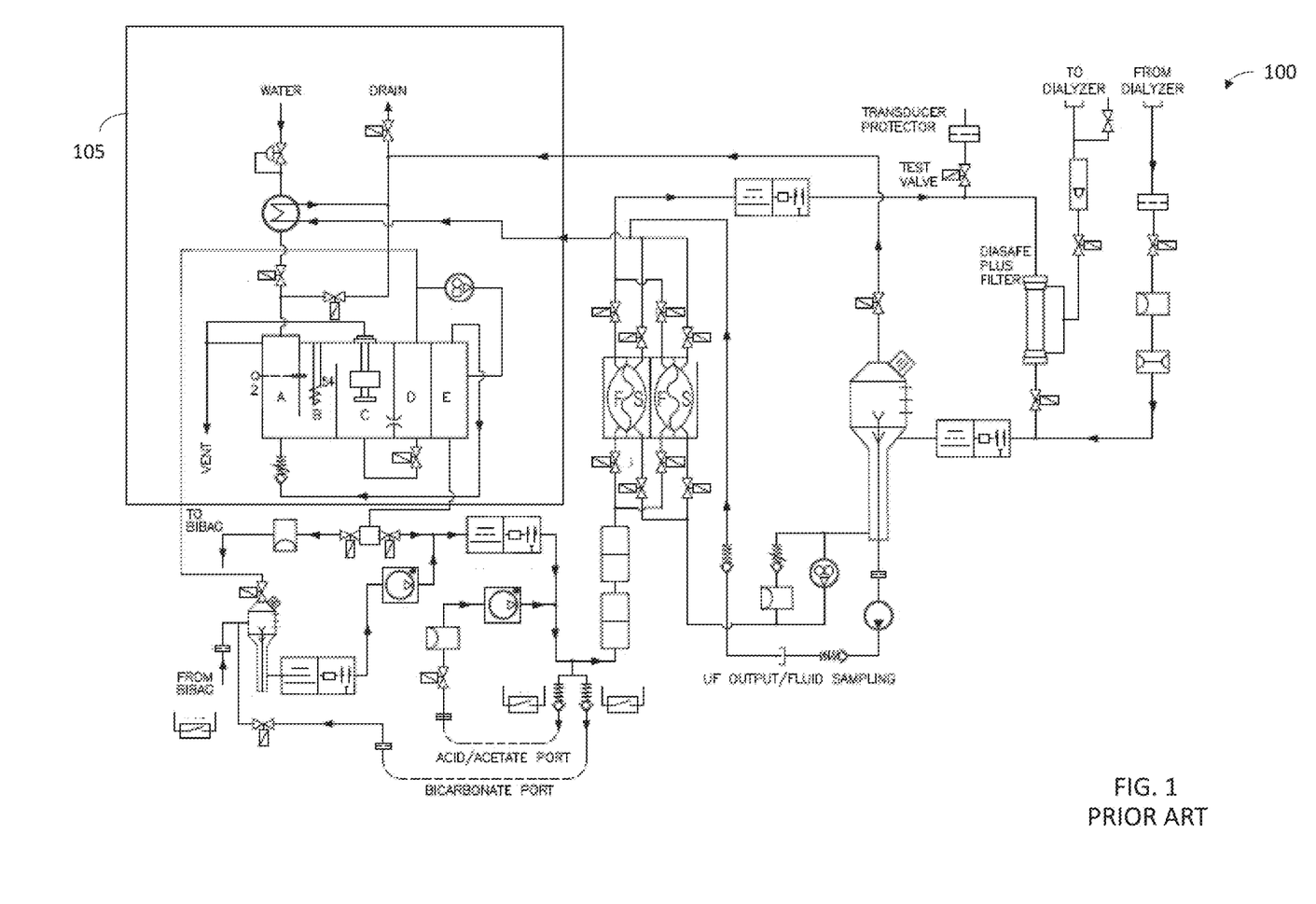
FIG. 1 illustrates a schematic diagram of an existing hemodialysis device.
Figure 2A:
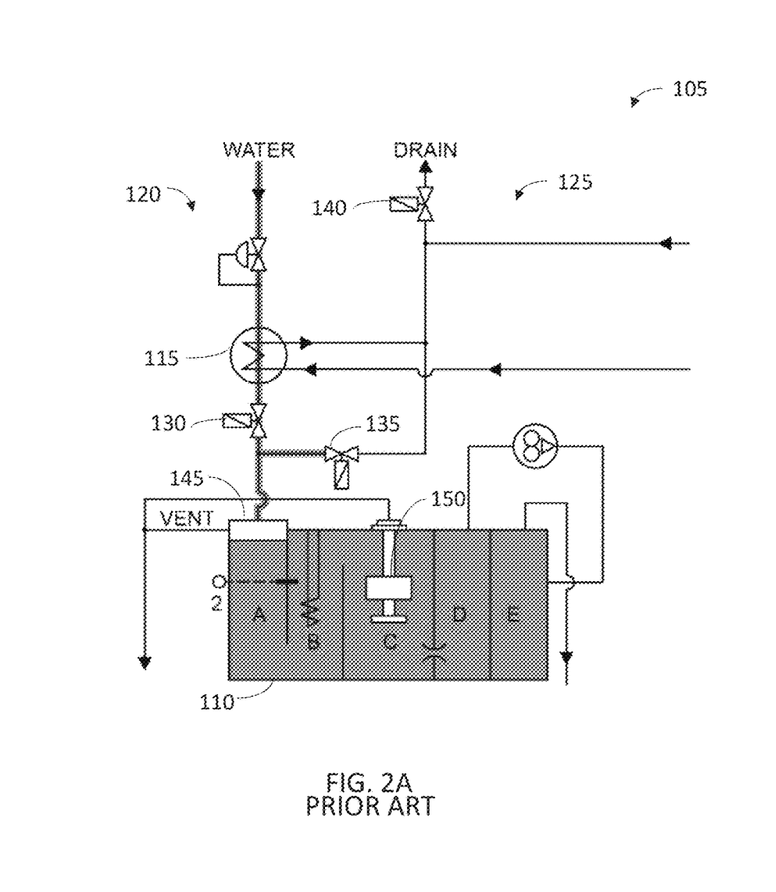
FIGS. 2A-2B illustrate a portion of the schematic diagram of FIG. 1 of an existing hemodialysis device.
Figure 2B:
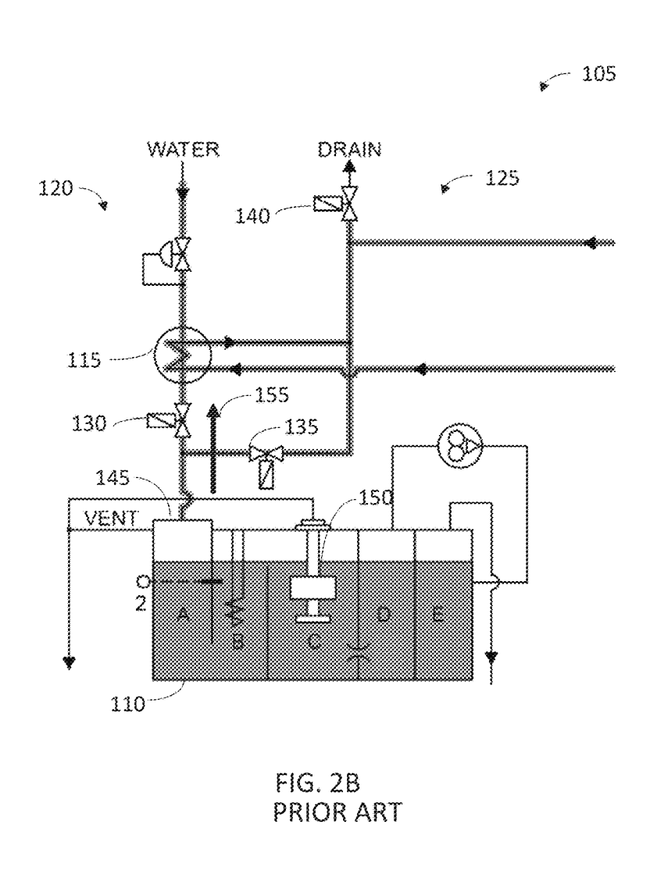

Referring to FIGS. 1, 2A, and 2B, a schematic diagram of an existing hemodialysis device is shown. FIGS. 2A and 2B show a portion 105 of the schematic diagram 100 illustrated in FIG. 1.

The hemodialysis device may include a hydrochamber 110 and a heat exchanger 115 in fluid communication with the hydrochamber 110. A water circuit 120 and a spent dialysate circuit 125 in the hemodialysis device provide fluid flow in the portion 105 of the schematic diagram. An external water source (not shown) may provide water to the water circuit 120. Water may flow through the heat exchanger 115 so that it is heated prior to entering the hydrochamber 110. A water inlet valve 130 may be disposed in the water circuit between the heat exchanger 115 and the hydrochamber 110. When the water inlet valve 130 is open, water may flow from the external water source into the hydrochamber 110. In embodiments, water may flow past an air gap 145 in the hydrochamber. The air gap 145 may prevent potential backflow of the water from the hydrochamber back through the water inlet valve 130.

The hydrochamber 110 may include a plurality of chambers 110A, 110B, 110C, 110D, and 110E. In an embodiment, water may enter a first chamber, e.g., chamber 110A and is heated in chamber 110B. Control of the water flow may occur in chamber 110C, for example, by including sensors and/or switches to monitor fluid in the hydrochamber. The fluid may be de-gassed or de-aerated in another chamber, e.g., 110D and/or 110E, so that balancing errors in the fluid are reduced. The fluid circuit is connected between the water inlet valve 130, the recirculation valve 135, and the hydrochamber 110.

As described above, during a dialysis operation or dialysis mode, backflow of fluid is prevented by the air gap between the water inlet valve 130 and the hydrochamber 110. Additionally, a recirculation valve 135 remains closed, so that the spent dialysate circuit 125 remains closed off from the water circuit 120. Potential patient contamination is thereby prevented should an external loss of water pressure occur. As shown in FIG. 2A, the highlighted flow line shows water flow from an external water source (not shown) through the heat exchanger 115, through the water inlet valve 130, and into the hydrochamber 110 past the air gap 145. With the recirculation valve 135 closed, the water circuit 120 is isolated from the spent dialysate circuit 125. To detect a loss of water pressure, as described above, one or more sensors 150 may be disposed in a chamber 110A-110E. In an embodiment, the sensor 150 may be a float to detect a fluid level in the hydrochamber 110. In response to a change in the fluid level in the hydrochamber 110, a controller of the hemodialysis device may output a warning, alarm, and/or automatic shut-down.

During a disinfectant operation, a disinfecting agent circulates from the spent dialysate circuit 125 to the hydrochamber 110 through the recirculation valve 135. In an embodiment, the disinfectant operation may be a chemical disinfection and/or rinse. In an embodiment, the disinfecting agent may be a disinfectant. Periodic disinfection of the fluid circuits cleans the tubing in the system of microorganisms.

A drain valve 140 may open at periodic time intervals to drain fluid out of the spent dialysate circuit, so that the disinfecting agent disinfects the drain valve 140. To replace the drained fluid volume, the water inlet valve 130 opens to flow water in through the water circuit 120. The water circuit 120 is kept at a positive pressure over the spent dialysate circuit 125, so that water will always flow from a higher pressure area to the lower pressure hydrochamber when the water inlet valve 130 is opened. For example, the water pressure may be 20 psi. However, if an external water source fails, the fluid pressure may drop in the water circuit 120. Thus, when the water inlet valve 130 is opened at the same time the recirculation valve 135 is opened during the disinfectant operation, the negative pressure in the water circuit 120 may result in a disinfecting agent back-flowing through the water inlet valve 130. As shown in FIG. 2B, the highlighted flow path shows fluid in the spent dialysate circuit as well as the water circuit. Backflow occurs by the negative pressure at the external water source drawing the disinfecting agent through the water inlet valve 130 in a direction of arrow 155 shown in FIG. 2B, resulting in contamination of the inlet portion of the water circuit 120 and potentially the external water source itself. As described above, such contamination may put patients at serious risk.

Figure 3:
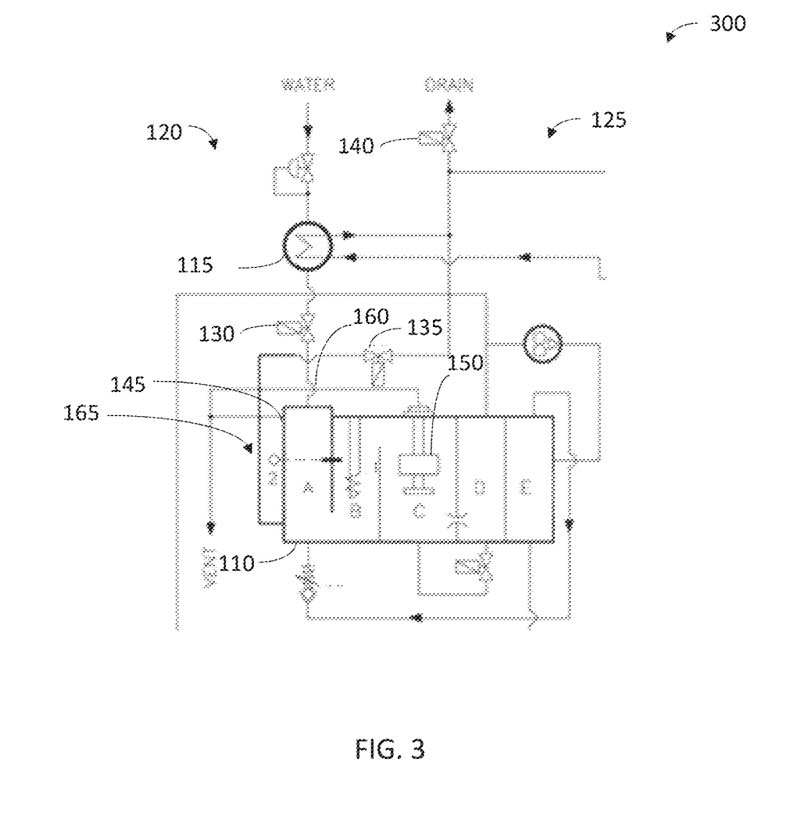
FIG. 3 illustrates a portion of a schematic diagram of a hemodialysis device according to an embodiment of the present invention.
Figure 4:
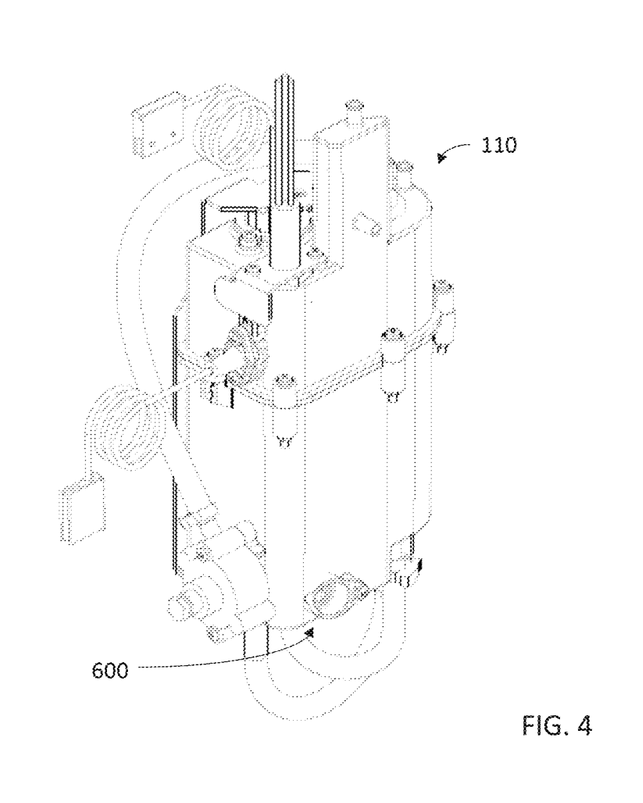
FIG. 4 illustrates a hydrochamber component of a hemodialysis device according to an embodiment of the present invention.

Referring now to FIG. 3, a portion 300 of a schematic diagram of a hemodialysis device according to an embodiment of the present invention is shown. The recirculation valve 135 is directly connected to the hydrochamber 110, so that a fluid flow path between the water inlet valve 130 and the recirculation valve 135 are independent of each other. For example, in an embodiment, a fluid flow path 160 may be between the water inlet valve 130 and the hydrochamber 110, and another, separate, fluid flow path 165 may be between the recirculation valve 135 and the hydrochamber 110.

During a disinfectant operation, the recirculation valve 135 is opened to flow a disinfecting agent from the spent dialysate circuit 125 to the hydrochamber 110 through the fluid flow path 165. When the drain valve 140 is opened at periodic time intervals, for example, every 30 seconds, a volume of fluid is drained. A disinfectant operation may last from 10 to 60 minutes. The drain valve 140 may be periodically opened while the disinfectant operation is ongoing, and may be pre-set, or pre-selected time intervals. The volume of fluid drained is replaced by substantially the same volume of flowing water through the water inlet valve 130 to the hydrochamber 110, past the air gap 145 in the fluid flow path 160. As described above, the air gap 145 prevents backflow of water from the hydrochamber 110 through the water inlet valve 130.

In the event of a loss of pressure at an external water source when the recirculation valve 135 is open during a disinfectant operation, disinfecting agent is prevented from flowing back through the water inlet valve 130 due to the independent fluid flow paths 160, 165. Thus, contamination is prevented and patient safety is ensured.

Referring now to FIGS. 4, 5A-5D, and 6A-6B, a hydrochamber 110 and components of a hemodialysis device according to an embodiment of the present invention are shown. As described above, the hemodialysis device may include a fluid flow to the hydrochamber 110 from an external water source (not shown). The recirculation valve 135 may be directly connected to the hydrochamber 110 via tubing including a dual valve manifold 500 at the recirculation valve 135 and a recirculation port 600 at the hydrochamber 110. In some embodiments, the tubing may be connected to the hydrochamber 110 below the air gap 145. Although the dual valve manifold 500 may be used to connect the recirculation valve 135 to the hydrochamber 110, any configuration to individually connect the recirculation valve 135 to the hydrochamber 110 and the water inlet valve 130 to the hydrochamber 110 is envisioned.

The dual valve manifold 500 may include a first channel 505 with a first end port 510 and a first valve connection 515, and a second channel 520 with a second end port 525 and a second valve connection 530. The first end port 510 of the first channel 505 may connect to the water inlet valve 130, and the first valve connection 515 of the first channel 505 may be connected to the hydrochamber 110, or vice versa. The second end port 525 of the second channel 520 may connect to the recirculation valve 135 and the second valve connection 530 of the second channel 520 may connect to the hydrochamber 110, or vice versa. The first and second channels 505, 520 may be formed in an "L" shape, with the dual valve manifold 500 being a rectangular shape, although any configurations that provide for independent and/or isolated flow paths between the water inlet valve 130 and the hydrochamber 110, on the one hand, and recirculation valve 135 and hydrochamber 110, on the other hand, are suitable. The dual valve manifold 500 may be formed of a plastic material, for example, polyethersulfone, to withstand corrosive fluids in the hemodialysis device.

Figure 5A:
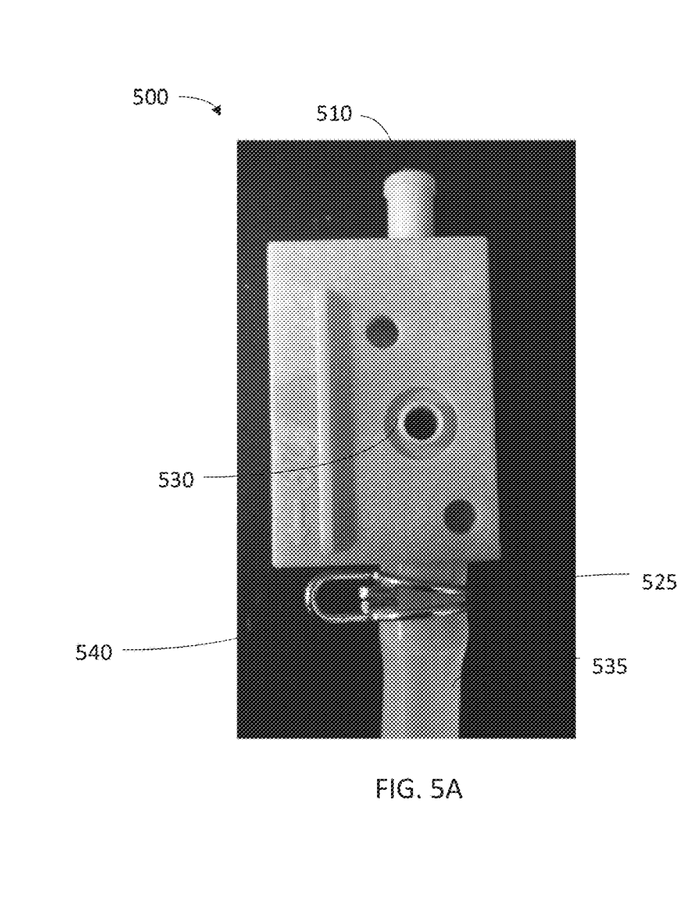
FIGS. 5A-5D illustrate a dual manifold valve of the hemodialysis device according to an embodiment of the present invention.
Figure 5B:
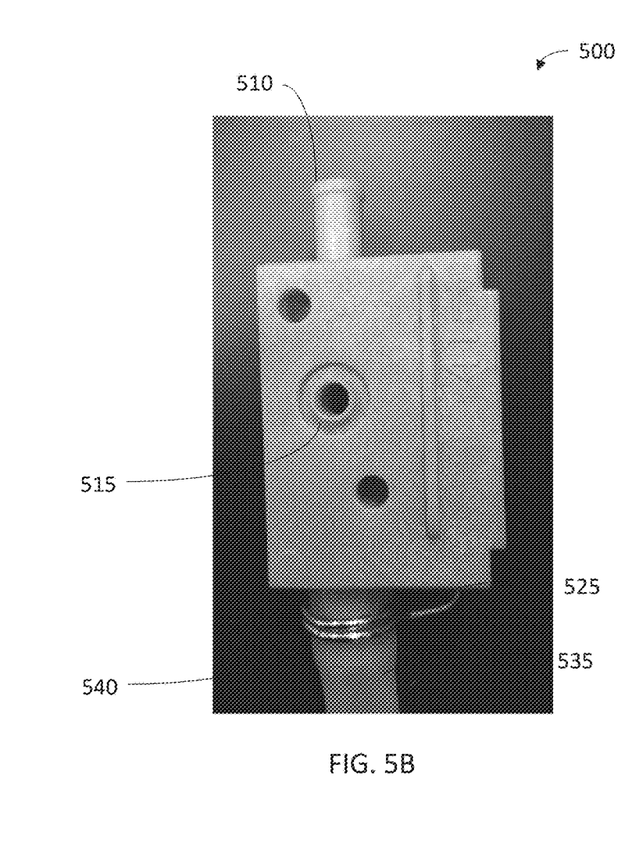
Figure 5C:
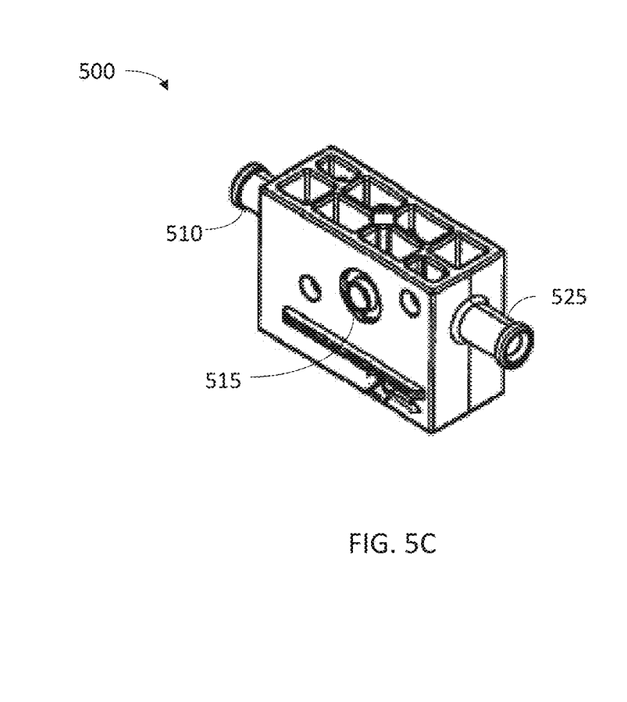
Figure 5D:
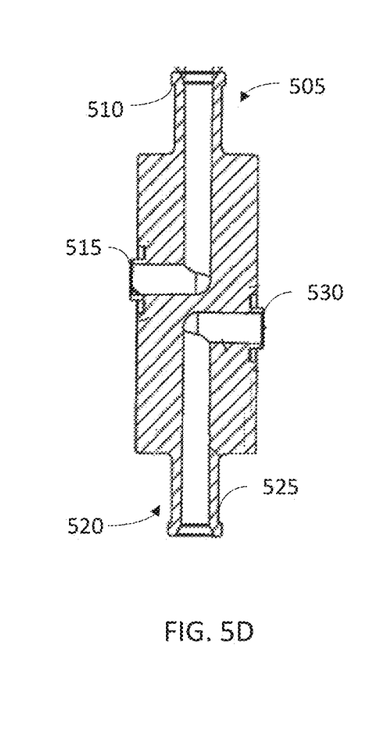

As shown in FIGS. 5A and 5B, tubing 535 may be connected to ports 510, 525. In an embodiment, the tubing may be secured by a fastener 540, such as a clip or clamp to secure the tubing to the ports 510, 525. The ports 510, 525 may be configured to fit within tubing, attached so that leaks are prevented. The first channel 505 and the second channel 520 may separate, independent flow paths to the hydrochamber, which are isolated by the configuration of the dual valve manifold 500. As more clearly shown in FIG. 5D, which is a sectional view of FIG. 5C, the dual valve manifold 500 provides for two paths to connect to the hydrochamber 110.

Figure 6A:
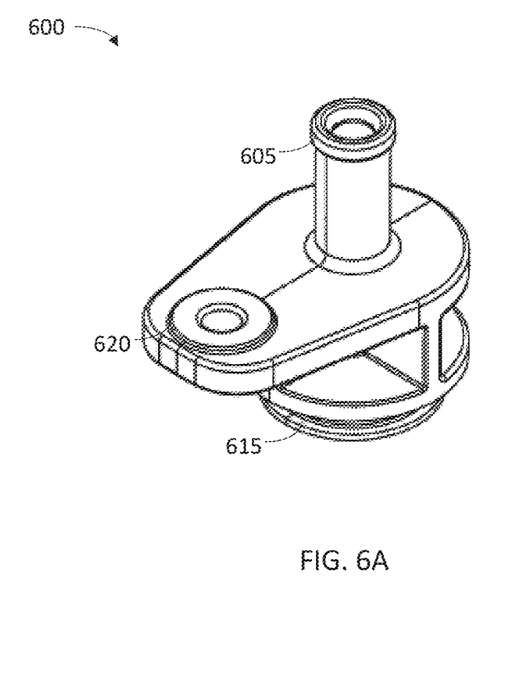
FIGS. 6A-6B illustrate a recirculation port of the hydrochamber of the hemodialysis device according to an embodiment of the present invention.
Figure 6B:
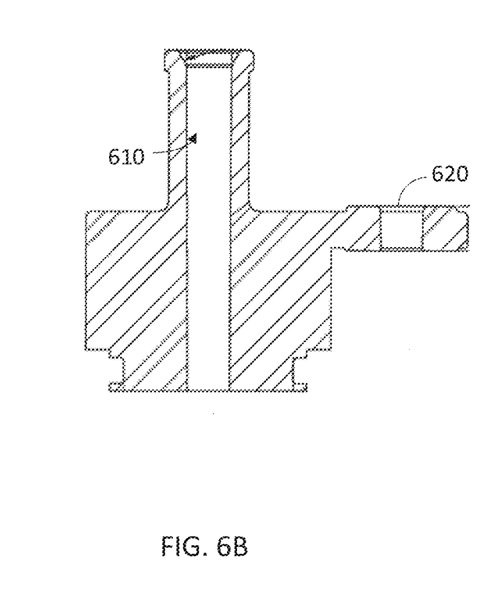

Referring now to FIGS. 6A, 6B, a recirculation port 600 may be disposed at the hydrochamber 110. The recirculation port 600 may include a connecting end 605 for tubing (not shown) to be attached. A flow path 610 through the recirculation port 600 allows for fluid to flow to the hydrochamber 110 through the tubing and the dual valve manifold 500 from the recirculation valve 135. A connecting end 615 is configured to join the recirculation port 600 to the hydrochamber 110. In an embodiment, a seal, for example, a ring seal, may be disposed between the hydrochamber 110 and the recirculation port 600 to prevent leakage. In an embodiment, an additional connector 620 may attach the recirculation port 600 to the hydrochamber 110. For example, additional connector 620 may be a hole to receive a screw, bolt, rivet, or other mechanical fastener.

The recirculation port 600 may be cylindrical or circular in shape. In an embodiment, the recirculation port 600 may be any shape permitting a fluid flow path 610. The recirculation port 600 may be formed of a plastic material, for example, polyethersulfone, to withstand corrosive fluids in the hemodialysis device.

Figure 7:
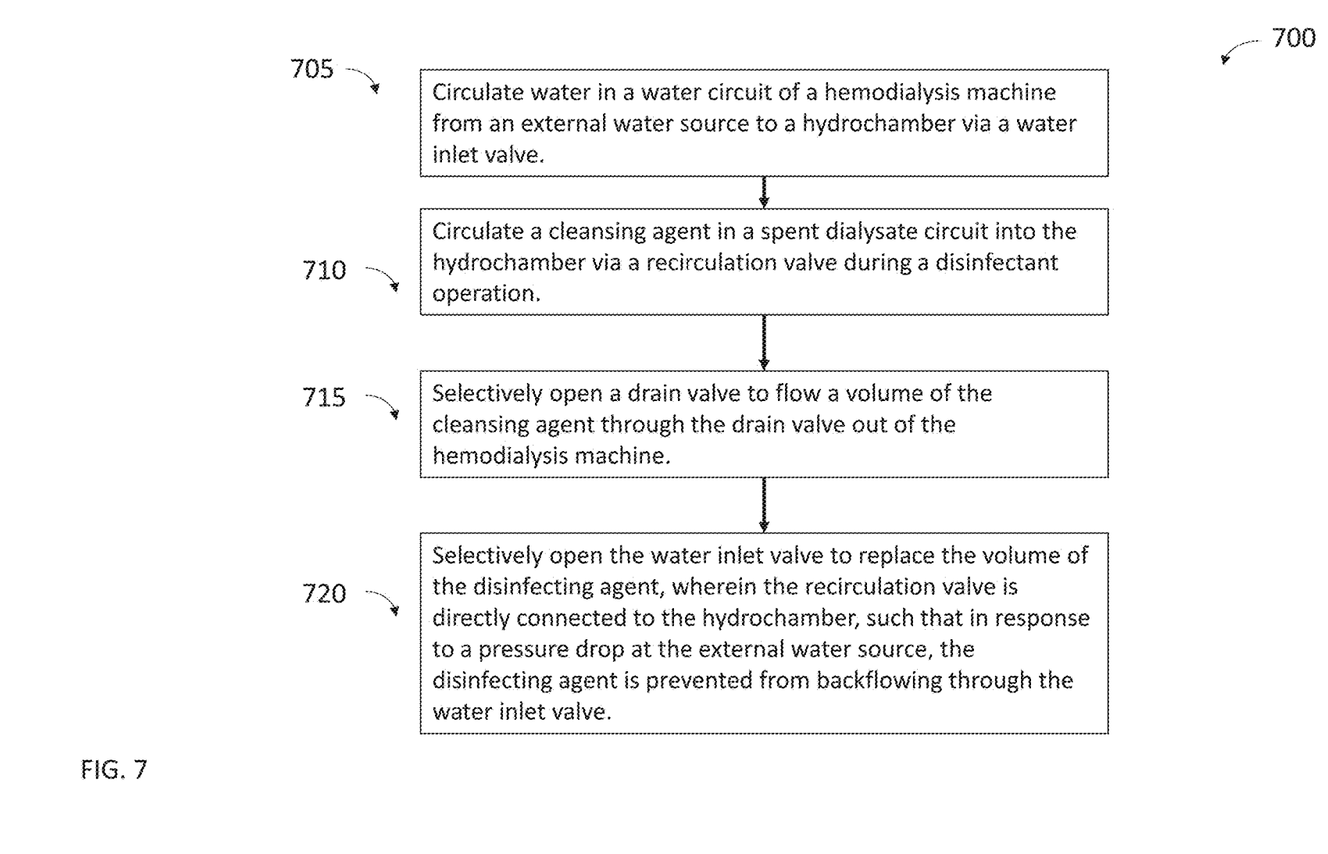
FIG. 7 illustrates a flow diagram of a method of preventing contamination in a hemodialysis device according to an embodiment of the present invention.

Referring now to FIG. 7, a flow diagram 700 of a method of preventing backflow in a hemodialysis device according to an embodiment of the present invention is shown. In step 705, the hemodialysis device circulates water in a water circuit from an external water source to a hydrochamber via a water inlet valve. At step 710, the hemodialysis device circulates a disinfecting agent in a spent dialysate circuit into the hydrochamber via a recirculation valve during a disinfectant operation. At step 715, the hemodialysis device selectively opens a drain valve to flow a volume of the disinfecting agent through the drain valve out of the hemodialysis device. At step 720, the hemodialysis device selectively opens the water inlet valve to replace the volume of the disinfecting agent. The recirculation valve is directly connected to the hydrochamber, such that in response to a pressure drop at the external water source, the disinfecting agent is prevented from back-flowing through the water inlet valve.

Figure 8:
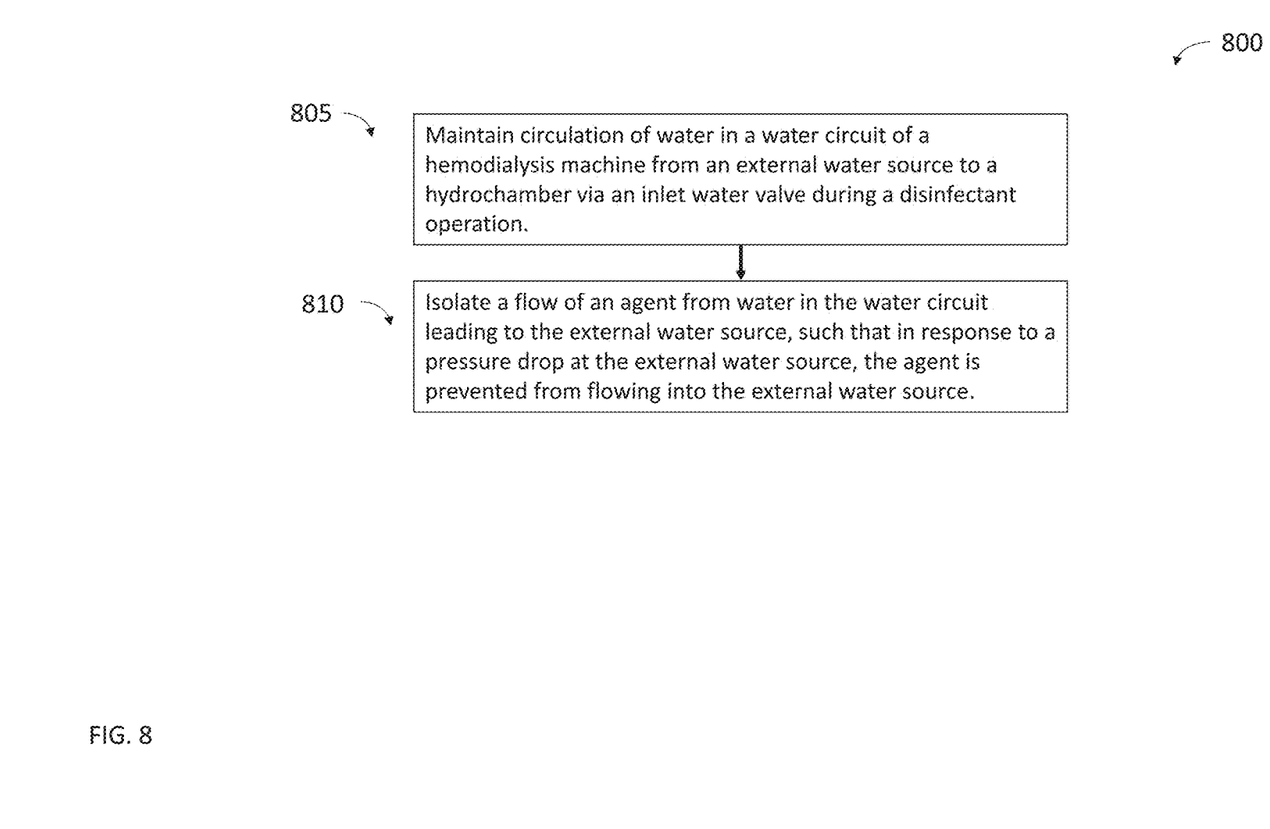
FIG. 8 illustrates a flow diagram of a method of preventing contamination in a hemodialysis device according to an embodiment of the present invention.

Referring now to FIG. 8, a flow diagram 800 of a method of preventing backflow in a hemodialysis device according to an embodiment of the present invention is shown. At step 805, the hemodialysis device maintains circulation of water in a water circuit from an external water source to a hydrochamber via a water inlet valve during a disinfectant operation. At step 810, the hemodialysis device isolates a flow of an agent from water in the water circuit leading to the external water source, such that in response to a pressure drop at the external water source, the agent is prevented from flowing into the external water source.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A hemodialysis system, comprising:
   a hydrochamber adapted to heat and remove air from water and to provide backflow protection, the hydrochamber including a first inlet located at a top portion thereof and a second inlet located at a bottom portion thereof;
   a water circuit for water to flow from an external water source into the hydrochamber via a water inlet valve, the water inlet valve being connected to the first inlet located at the top portion of the hydrochamber via a first fluid flow path;

a spent dialysate circuit for a disinfecting agent to flow to the hydrochamber via a recirculation valve during a disinfectant operation; and a drain valve disposed in the spent dialysate circuit;

wherein during the disinfectant operation, the hemodialysis system is adapted to replace a volume of the disinfecting agent exiting the spent dialysate circuit via the drain valve with a substantially equal volume of water via the water inlet valve; and wherein the recirculation valve is directly connected to the hydrochamber via a second fluid flow path connected to the second inlet located at the bottom portion of the hydrochamber, the second fluid flow path being separate and independent of the first fluid flow path such that in response to a pressure drop at the external water source, the disinfecting agent is prevented from back-flowing through the water inlet valve.

2. The hemodialysis system according to claim 1, wherein the recirculation valve is directly connected to the hydrochamber via tubing including a dual valve manifold at the hydrochamber and a recirculation port at the recirculation valve.

3. The hemodialysis system according to claim 2, wherein the dual valve manifold includes a first channel with a first end port, and a second channel with a second end port, the first end port connecting to the water inlet valve, and the second end port connecting to the recirculation valve.

4. The hemodialysis system according to claim 3, wherein the first channel and the second channel are separate channels in the dual valve manifold such that each flow path is isolated.

5. The hemodialysis system according to claim 2, wherein the recirculation port connects tubing between the recirculation valve and the dual valve manifold at the hydrochamber.

6. The hemodialysis system according to claim 1, further comprising an air gap between the water inlet valve and the hydrochamber.

7. The hemodialysis system according to claim 6, wherein during a dialysis operation mode, backflow of water is prevented by the air gap, and the recirculation valve is closed, such that in response to the pressure drop at the external water source, a controller generates a signal alarm.

8. The hemodialysis system according to claim 7, wherein a float in the hydrochamber senses the pressure drop at the external water source.

9. The hemodialysis system according to claim 1, wherein the drain valve is adapted to open at a pre-selected time interval during the disinfectant operation.

10. The hemodialysis system according to claim 9, wherein the drain valve is adapted to open at 30 second time intervals.

11. The hemodialysis system according to claim 1, further comprising a heat exchanger in fluid communication with the hydrochamber.

12. The hemodialysis system according to claim 1, wherein the disinfecting agent is a disinfectant, and the disinfectant operation is at least one of a chemical disinfection and/or a rinse.

13. A hemodialysis device preventing backflow contamination during a loss of pressure at an external water source, the hemodialysis device comprising:

a water inlet valve adapted and configured to couple to a water circuit for water to flow to a hydrochamber from the external water source;

a recirculation valve adapted and configured to couple to a fluid circuit for a disinfecting agent to flow to the hydrochamber during a disinfectant operation;

an air gap located between the water inlet valve and the hydrochamber; and a dual valve manifold, the dual valve manifold including a first channel with a first end port, and a second channel with a second end port, the first end port connecting to the water inlet valve via first tubing and the second end port connecting to the recirculation valve via second tubing, the second tubing being separate and independent of the first tubing;

wherein the first tubing is connected to a first inlet located in the hydrochamber, the second tubing being connected to a second inlet located in the hydrochamber, the second inlet being positioned below the air gap;

wherein the first channel and the second channel are separate channels in the dual valve manifold such that each flow path is isolated; and wherein the recirculation valve is directly connected to the hydrochamber via the second tubing, such that in response to pressure loss at the external water source, the disinfecting agent is prevented from back-flowing through the water inlet valve.

14. The hemodialysis device according to claim 13, further comprising a recirculation port disposed at the hydrochamber, wherein the recirculation port connects the second tubing between the recirculation valve via the dual valve manifold and the hydrochamber.

* * * * *